United States Patent
Kloth et al.

(10) Patent No.: US 9,828,306 B2
(45) Date of Patent: *Nov. 28, 2017

(54) PROCESSES FOR THE PREPARATION OF AN OLEFINIC PRODUCT

(71) Applicant: SHELL OIL COMPANY, Houston, TX (US)

(72) Inventors: Antonius Gijsbertus Johannes Kloth, Vaals (NL); Sivakumar Sadasivan Vijayakumari, Gonzales, LA (US); Jeroen Van Westrenen, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/439,292

(22) PCT Filed: Oct. 29, 2013

(86) PCT No.: PCT/EP2013/072629
§ 371 (c)(1),
(2) Date: Apr. 29, 2015

(87) PCT Pub. No.: WO2014/067957
PCT Pub. Date: May 8, 2014

(65) Prior Publication Data
US 2015/0291484 A1    Oct. 15, 2015

(30) Foreign Application Priority Data

Oct. 31, 2012  (EP) .................................. 12190907
Nov. 13, 2012  (EP) .................................. 12192413

(51) Int. Cl.
*C07C 1/20* (2006.01)
*C10G 9/00* (2006.01)
*C07C 4/04* (2006.01)

(52) U.S. Cl.
CPC .................. *C07C 1/20* (2013.01); *C07C 4/04* (2013.01); *C10G 9/00* (2013.01); *C07C 2529/06* (2013.01); *Y02P 30/42* (2015.11)

(58) Field of Classification Search
CPC .. C07C 1/20; C07C 11/02; C07C 4/06; C10G 2300/1011; C10G 2300/104; C10G 2300/1044; C10G 2300/1051; C10G 2300/1059; C10G 2300/1081; C10G 2300/1085; C10G 2400/02; C10G 2400/20; C10G 2400/22; C10G 45/08; C10G 45/12

See application file for complete search history.

(56) References Cited

U.S. PATENT DOCUMENTS

| | | |
|---|---|---|
| 4,179,474 A | 12/1979 | Beuther et al. |
| 4,567,029 A | 1/1986 | Wilson et al. |
| 5,484,755 A | 1/1996 | Lopez |
| 6,403,854 B1 * | 6/2002 | Miller .................. B01D 3/143 585/638 |
| 6,870,072 B2 * | 3/2005 | Lumgair .................. C07C 1/20 208/161 |
| 7,329,790 B2 | 2/2008 | Bjorklund et al. |
| 2004/0152939 A1 | 8/2004 | Pettigrew et al. |
| 2004/0267069 A1 | 12/2004 | Ding et al. |
| 2004/0267075 A1 | 12/2004 | Lumgair, Jr. et al. |
| 2005/0038304 A1 * | 2/2005 | Van Egmond ............ C07C 1/20 585/324 |
| 2007/0103380 A1 | 5/2007 | Weste |
| 2007/0155999 A1 | 7/2007 | Pujado et al. |
| 2008/0161616 A1 | 7/2008 | Miller |
| 2009/0048475 A1 | 2/2009 | Powers |

FOREIGN PATENT DOCUMENTS

| | | |
|---|---|---|
| CN | 1055380 A | 10/1991 |
| CN | 1809519 A | 7/2006 |
| WO | 0200579 | 1/2002 |
| WO | 03037834 | 5/2003 |
| WO | 03104170 | 12/2003 |
| WO | 2006020083 | 2/2006 |
| WO | 2009045186 A1 | 4/2009 |
| WO | 2009085565 | 7/2009 |

* cited by examiner

Primary Examiner — Sharon Pregler (57) ABSTRACT

The invention provides a process for preparing an olefin, comprising:

(a) reacting an oxygenate, in a reaction zone in the presence of a molecular sieve catalyst, at a temperature from 350 to 1000° C., to produce a effluent stream, comprising at least oxygenate, olefin, water and acidic by-products;

(b) cooling the reaction effluent stream by an indirect heat exchange to a temperature greater than the dew point temperature of effluent stream;

(c) further rapidly cooling the effluent stream to a temperature lower than the dew point temperature of the effluent stream by direct injection of an aqueous liquid into the effluent stream, to form a quench effluent stream; and (d) passing the quench effluent stream into a quench tower and contacting the quench effluent stream with a second aqueous liquid in the presence of at least one set of internals, to produce a quench tower gaseous stream comprising the olefin.

10 Claims, 5 Drawing Sheets

PROCESSES FOR THE PREPARATION OF AN OLEFINIC PRODUCT

PRIORITY CLAIM

The present application is the National Stage (§371) of International Application No. PCT/EP2013/072629, filed Oct. 29, 2013, which claims priority from European Patent Application No. 12190907, filed Oct. 31, 2012 and 12192413.8, filed Nov. 13, 2012, incorporated herein by reference.

FIELD OF THE INVENTION

The present invention relates to a process for the preparation of an olefinic product, such as one or both of ethylene and propylene, from an oxygenate feedstock.

BACKGROUND OF THE INVENTION

Conventionally, ethylene and propylene are produced via steam cracking of paraffinic feedstocks comprising ethane or ethane/propane mixtures, known as gas cracking, or propane, butane, naphtha, NGL (natural gas liquids), condensates, kero, gas oil and hydrowax, known as naphtha cracking. An alternative route to ethylene and propylene is an oxygenate-to-olefin (OTO) process. Interest in OTO processes for producing ethylene and propylene is growing in view of the increasing availability of natural gas. Methane in the natural gas can be converted into, for instance, methanol or dimethylether (DME), both of which are suitable feedstocks for an OTO process.

In an OTO process, an oxygenate such as methanol or dimethylether is provided to a reaction zone of a reactor comprising a suitable conversion catalyst and is converted to ethylene and propylene. In addition to the desired ethylene and propylene, a substantial part of the oxygenate such as methanol is converted to higher hydrocarbons including C4+ olefins, paraffins and carbonaceous deposits on the catalyst. The catalyst is continuously regenerated to remove a portion of the carbonaceous deposits by methods known in the art, for example heating the catalyst with an oxygen-containing gas such as air or oxygen.

The effluent from the reactor, comprising the olefins, any unreacted oxygenates such as methanol and dimethylether and other reaction products such as water, once separated from the bulk of the catalyst, may then be treated to provide separate component streams. In order to increase the ethylene and propylene yield of the process, the C4+ olefins component stream may be recycled to the reaction zone or alternatively further cracked in a dedicated olefin cracking zone to produce further ethylene and propylene.

Following reaction, the reaction effluent stream must be cooled before being treated to provide separate component streams. Conventionally, the reaction effluent stream is cooled to around 140 to 350° C. using one or more heat exchangers, often one or more transfer line exchangers (TLEs), before being contacted with a cooled aqueous stream in a quench tower. A quench tower comprises at least one set of internals such as packing and/or trays. In usual operation, the gaseous stream to be quenched is fed into the quench tower below the internals and one or more cooled aqueous stream is fed into the quench tower above the internals. Thus, the gaseous stream travels upwards through the quench tower and is brought into contact with the one or more cooled aqueous stream travelling downwards through the tower (counter-currently to the gaseous stream). An aqueous stream containing condensed materials is removed at the bottom of the tower, cooled and recycled. The cooled gaseous stream is removed from the top of the quench tower.

Acidic by-products, such as formic acid and acetic acid, are formed in the reaction zone and are present in the reaction effluent stream. This formation of acidic by-products also continues as the reaction effluent stream is cooled to around 200° C. in one or more heat exchangers. As the gaseous reaction effluent stream is then further cooled, the components begin to condense to form liquids. The first drops of liquid formed are highly acidic (pH as low as 1 or 2), due to the presence of the acidic by-products. Such low pH material leads to corrosion of the process equipment. This corrosion is known as 'dew point corrosion' as it occurs at the dew point, which is the temperature at which a vapour in a volume of gas will condense into liquid, for a certain pressure.

Due to the high temperatures in the reaction zone and the acidity of the catalyst, a portion of the oxygenates such as methanol may unavoidably decompose thermally or catalytically into oxides of carbon, i.e. carbon monoxide and carbon dioxide in the gaseous form. Carbon dioxide generated during the OTO process is an acidic gas which is, thus, present in the effluent from the reactor. In order to prevent contamination of the olefinic product and problems associated with the formation of solid carbon dioxide during the separation of the olefinic product into olefinic component streams, which may be carried out at cryogenic temperatures, carbon dioxide should be removed from the reaction effluent and from the gaseous effluent from the cooling process before separation into olefinic component streams, for instance by treating with a caustic solution.

Carbonyl compounds, such as aldehydes and ketones, particularly formaldehyde and acetaldehyde, are commonly generated by the catalyst in side reactions and are also found in the effluent from the reactor. High CO concentrations and long residence times at temperatures in the range of from 100 to 350° C., particularly in the presence of metal surfaces, will further promote the formation and accumulation of aldehydes. Thus, in a conventional set-up, comprising one or more TLEs followed by a quench tower, a considerable amount of aldehyde production occurs in the pipes connecting the TLEs to the quench tower.

These carbonyl compounds may absorb and build up in the caustic solution used to remove carbon dioxide and other acid gases downstream of the quench section. The basic components of the caustic solution, such as hydroxide ions, can catalyse the aldol condensation and subsequent dehydration reactions of particularly acetaldehyde to form unsaturated aldehydes such as acrolein, especially at higher pH, such as a pH of greater than 9. Unsaturated aldehydes will polymerise when allowed to accumulate in the caustic solution and if the aldol condensation reaction is left unchecked, viscous oily polymers, polymer films and lumbs can be formed. These are known as 'red oil', are insoluble in the caustic solution and can deposit on equipment internals, causing severe fouling and blockages.

Catalyst fines are usually present in the reaction effluent stream, even after separation of the bulk of the catalyst. With continuous recycling of the aqueous streams (into which the fines will pass), any catalyst fines present in the reaction effluent stream build up on internals, causing blockages.

It would be desirable to avoid the problems of dew point corrosion, red oil make and catalyst fine blockages in a process for the preparation of olefinic products from oxygenates.

SUMMARY OF THE INVENTION

Accordingly, the present invention provides a process for the preparation of an olefinic product, the process comprising the steps of:
(a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
(b) cooling the reaction effluent stream by means of an indirect heat exchange to a temperature greater than the dew point temperature of reaction effluent stream;
(c) further rapidly cooling the reaction effluent stream to a temperature lower than the dew point temperature of the reaction effluent stream by direct injection of a first aqueous liquid into the reaction effluent stream, to form a quench effluent stream; and
(d) passing the quench effluent stream into a quench tower and contacting the quench effluent stream with a second aqueous liquid in the presence of at least one set of quench tower internals, to produce a quench tower gaseous stream comprising the olefinic product.

DETAILED DESCRIPTION OF THE INVENTION

The present invention addresses the problems indicated by subjecting the reaction effluent stream to a direct quench with an aqueous liquid after initial cooling in one or more heat exchangers. The direct quench rapidly cools the reaction effluent stream in the presence of a large quantity of water, thus preventing the formation of highly acidic droplets. The rapid cooling cuts down residence time at temperatures which encourage aldehyde make and, therefore, prevents further aldehyde formation at this stage of the process and reduces red oil make in the basic environment of the caustic wash tower. Further cooling and separation is then carried out in a quench tower downstream of the quench section.

Since a large part of the cooling is carried out in the direct quench step, less cooling is required in downstream equipment. Further, since the temperature is lower, the gas volume is reduced and the downstream equipment can be smaller. Another benefit is that the direct quench system can be designed for a very high turndown which is much higher than for a heat exchanger or quench tower.

In step (b) the reaction effluent stream is cooled by means of an indirect heat exchange to recover the heat contained in the reactor effluent. Typically, the reaction effluent stream is indirectly contacted with a liquid stream, which is at a lower temperature, in a heat exchanger. The liquid stream is suitably a process stream, for instance a reactor feed, or a water stream. The heat exchanger may be of any type known in the art, for instance a transfer line exchanger (TLE) and/or a feed/effluent exchanger. Preferably, a shell and tube type heat exchanger is used.

In step (b) the reaction effluent stream is cooled to a temperature greater than the dew point of the reaction effluent stream. Preferably the reaction effluent stream is cooled to a temperature of no less that 140° C., more preferably no less than 150° C., most preferably no less than 160° C. Preferably, the reaction effluent stream is cooled in step (b) to a temperature of at most 370° C., more preferably at most 320° C., more preferably at most 270° C., more preferably at most 250° C., even more preferably at most 240° C., even more preferably at most 220° C., even more preferably at most 200° C., even more preferably at most 190° C., most preferably at most 180° C.

The reaction effluent stream is further cooled in step (c) by injection of an aqueous liquid directly into the reaction effluent stream. The aqueous liquid is preferably water. It may suitably be fresh water, but preferably is a recycled stream from a later stage of the process for the preparation of an olefinic product.

Suitably, the aqueous liquid is at a temperature of at least 10° C., preferably at least 20° C., most preferably at least 25° C. Suitably the aqueous liquid is at a temp of at most 65° C., preferably at most 50° C., more preferably at most 40° C., most preferably at most 35° C.

The term 'direct injection' as used herein, indicates that the aqueous liquid is provided straight into the reaction effluent stream by a quench fitting suitable for dispersing the water into fine droplets, effectively forcing the liquid as fine droplets into the gas stream. The injection of the aqueous stream is co-current to the direction of flow of the reaction effluent stream.

The aqueous liquid is injected into the reaction effluent stream by means of a quench fitting. The quench fitting may be any means known in the art capable of rapidly introducing a large quantity of water directly into a gaseous stream, but suitably comprises a spray nozzle.

In one embodiment, the quench fitting comprises aqueous liquid injection facilities wherein the aqueous liquid is injected directly into a pipe or other conduit transporting the reaction effluent stream from the reactor and/or heat exchangers downstream of the reactor.

In one embodiment, spray nozzles are located in the sides of the conduit such that the aqueous liquid is injected directly into the conduit transporting the reaction effluent stream.

The aqueous stream is injected into the reaction effluent stream such that the mass ratio of the aqueous stream to be injected to the total contents of the reaction effluent stream is preferably at least 3:1, more preferably at least 4:1, most preferably at least 5:1. Preferably, the mass ratio of the aqueous stream to be injected to the total contents of the reaction effluent stream is at most 20:1, more preferably at most 15:1, even more preferably at most 10:1, most preferably at most 8:1. After cooling in step (c) the quench effluent stream must be at a temperature below the dew point temperature of the reaction effluent stream. Preferably the quench effluent stream is at a temperature of no more than 100° C., more preferably less than 100° C., more preferably no more than 95° C., most preferably no more than 90° C., most preferably no more than 85° C. Preferably, the quench effluent stream is at a temperature of at least 30° C., more preferably at least 40° C., more preferably at least 50° C., even more preferably at least 60° C., even more preferably at least 65° C., even more preferably at least 70° C., even more preferably at least 80° C., most preferably at most 85° C.

After cooling in step (c), the quench effluent stream is then fed into a quench tower at a point below any internals. The term internals as used herein preferably refers to packing and/or trays.

Gaseous material in the quench effluent stream will then pass upwards through the quench tower and contact a second aqueous liquid which is fed into the quench tower at one or more points above at least one set of internals. Preferably, the second aqueous liquid is fed into the quench tower at one or more points above each set of internals. After contacting the second aqueous liquid, the resultant quench tower gaseous stream is removed from the top of the quench tower.

All other materials present in the quench tower will pass to the bottom of the quench tower where separation of the different materials can occur. This separation can be achieved in the quench tower itself or the materials may be passed to a separate separation vessel, such as a knockout drum, a decanter or settler.

Streams to be separated include solids, preferably in the form of a slurry, an oxygenates containing liquid stream, a liquid hydrocarbons stream and further aqueous materials. The separated further aqueous materials are preferably recycled with cooling for use as the second aqueous liquid. The oxygenates containing liquid stream can be further separated to provide an oxygenate recovery stream for recycle as an oxygenate co-feed in the oxygenate reaction zone and a further aqueous recycle stream that can be cooled and used as the first aqueous liquid.

Reference herein to an oxygenate feedstock is to an oxygenate-comprising feedstock. In the oxygenate (or OTO) reaction zone, at least part of the feedstock is converted into a product containing one or more olefins, preferably including lower olefins, in particular ethylene and typically propylene.

The oxygenate used in the process is preferably an oxygenate which comprises at least one oxygen-bonded alkyl group. The alkyl group preferably is a C1-C5 alkyl group, more preferably C1-C4 alkyl group, i.e. comprises 1 to 5 or 1 to 4 carbon atoms respectively; more preferably the alkyl group comprises 1 or 2 carbon atoms and most preferably one carbon atom. Examples of oxygenates that can be used in the oxygenate feedstock include alcohols and ethers. Examples of preferred oxygenates include alcohols, such as methanol, ethanol, propanol; and dialkyl ethers, such as dimethyl ether, diethyl ether, methylethyl ether. Preferably, the oxygenate is methanol or dimethyl ether, or a mixture thereof.

Preferably, the oxygenate feedstock comprises at least 50 wt % of oxygenate, in particular methanol and/or dimethyl ether, based on total hydrocarbons, more preferably at least 70 wt %.

An oxygenate co-feed, comprising oxygenate recovered or produced in the process downstream of step (d) of the process of the present invention, such as an oxygenate recovered stream, may also be supplied, as discussed below. Such a stream may contain methanol, dimethyl ether and/or MTBE.

A diluent, such as water or steam, may also be provided to the oxygenate reaction zone. The molar ratio of oxygenate to diluent may be between 10:1 and 1:10, preferably between 4:1 and 1:2, in particular when the oxygenate is methanol and the diluent is water (typically steam).

Preferably, in addition to the oxygenate and diluent, an olefinic co-feed is provided along with and/or as part of the oxygenate feedstock. Reference herein to an olefinic co-feed is to an olefin-comprising co-feed.

The olefinic co-feed preferably comprises C4+ olefins i.e. C4 and higher olefins, more preferably C4 and C5 olefins.

In one preferred embodiment of the present invention, the olefinic co-feed comprises at least 30 wt %, preferably at least 50 wt %, more preferably at least 70 wt % of C4 hydrocarbon species. In this embodiment, the remainder of the olefinic co-feed comprises at least 70 wt %, more preferably at least 80 wt %, even more preferably at least 90 wt % C5 hydrocarbon species.

In a second preferred embodiment of the present invention, the olefinic co-feed comprises at least 50 wt %, preferably at least 70 wt % of C5 hydrocarbon species. In this embodiment, the remainder of the olefinic co-feed comprises at least 70 wt %, more preferably at least 80 wt %, even more preferably at least 90 wt % C4 hydrocarbon species.

Of the C4 hydrocarbon species present in the olefinic co-feed, preferably at least 35 wt %, more preferably at least 50 wt %, more preferably at least 75 wt % are olefins.

Of the C5 hydrocarbon species present in the olefinic co-feed, preferably at least 30 wt %, more preferably at least 45 wt % are non-cyclic olefins.

In order to maximize production of ethylene and propylene, it is desirable to maximize the recycle of C4 olefins in the effluent of the OTO process. This can be done by recycling at least part of the C4+ hydrocarbon fraction, preferably C4-C5 hydrocarbon fraction, more preferably C4 hydrocarbon fraction, in the OTO effluent. However, a certain part thereof, such as between 1 and 5 wt %, can be withdrawn as purge, since otherwise saturated hydrocarbons, in particular C4s (normal and iso butane) may build up in the process, which are substantially not converted under the OTO reaction conditions. Preferably, at least 70 wt % of the olefinic co-feed, during normal operation, is formed by a recycle stream of a C4+ hydrocarbon fraction from the OTO reaction effluent. Preferably, at least 90 wt % of olefinic co-feed, based on the whole olefinic co-feed, is formed by such recycle stream.

The preferred molar ratio of oxygenate in the oxygenate feedstock to olefin in the olefinic co-feed provided to the oxygenate reaction zone depends on the specific oxygenate used and the number of reactive oxygen-bonded alkyl groups therein. Preferably the molar ratio of oxygenate to olefin in the total feed lies in the range of 20:1 to 1:10, more preferably in the range of 18:1 to 1:5, still more preferably in the range of 15:1 to 1:3, even still more preferably in the range of 12:1 to 1:3.

A variety of OTO processes are known for converting oxygenates, such as for instance methanol or dimethyl ether to an olefin-containing product, as already referred to above. One such process is described in WO 2006/020083. Processes integrating the production of oxygenates from synthesis gas and their conversion to light olefins are described in US 20070203380 and US 20070155999.

Catalysts suitable for converting the oxygenate feedstock comprise molecular sieve. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more $[SiO_4]$, $[AlO_4]$ and/or $[PO_4]$ tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico) aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably, the substituted metal atom (Me) is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a silica-to-alumina ratio, SAR, of at least 60, preferably at least 80. More preferred MFI-type zeolites have a silica-to-alumina ratio in the range of from 60 to 150, more preferably of from 80 to 100, Particular catalysts include catalysts comprising one or more zeolites having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50 wt %. of such zeolites based on total zeolites in the catalyst. In one embodiment, the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05 to 10 wt % based on the weight of the formulated catalyst. A particularly preferred catalyst comprises phosphorus and MEL or MFI-type zeolite having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

It is preferred that molecular sieves in the hydrogen form are used in the oxygenate conversion catalyst, e.g., HZSM-22, HZSM-23, and HZSM-48, HZSM-5. Preferably at least 50% w/w, more preferably at least 90% w/w, still more preferably at least 95% w/w and most preferably 100% of the total amount of molecular sieve used is in the hydrogen form. It is well known in the art how to produce such molecular sieves in the hydrogen form.

The reaction conditions of the oxygenate conversion, include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Preferably, the oxygenate feedstock is preheated to a temperature in the range of from 200 to 550° C., more preferably 250 to 500° C. prior to contacting with the molecular sieve-comprising catalyst.

The catalyst particles used in the process can have any shape known to the skilled person to be suitable for this purpose, and can be present in the form of spray dried catalyst particles, spheres, tablets, rings, extrudates, etc. Extruded catalysts can be applied in various shapes, such as, cylinders and trilobes. Spray-dried particles allowing use in a fluidized bed or riser reactor system are preferred. Spherical particles are normally obtained by spray drying. Preferably the average particle size is in the range of 1-200 μm, preferably 50-100 μm.

Although the C4+ hydrocarbon fraction in the reaction effluent may be recycled as an olefinic co-feed as discussed above, in an alternative embodiment, at least part of the olefins in the C4+ hydrocarbon fraction are converted to ethylene and/or propylene by contacting the C4+ hydrocarbon fraction in a separate unit with a molecular sieve-comprising catalyst, particularly a zeolite-comprising catalyst. This is particularly preferred where molecular sieve-comprising catalyst in the OTO process comprises a least one SAPO, AlPO, or MeAlPO type molecular sieve, preferably SAPO-34. These catalysts are less suitable for converting C4+ olefins.

Preferably, the C4+ hydrocarbon fraction is contacted with the zeolite-comprising catalyst at a reaction temperature of 350 to 1000° C., preferably from 375 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Optionally, the stream comprising C4+ olefins also contains a diluent. Examples of suitable diluents include, but are not limited to, liquid water or steam, nitrogen, argon, paraffins and methane. Under these conditions, at least part of the olefins in the C4+ hydrocarbon fraction are converted to further ethylene and/or propylene. The further ethylene and/or propylene may be combined with the further ethylene and/or propylene obtained directly from the oxygenate reaction zone. Such a separate process step directed at converting C4+ olefins to ethylene and propylene is also referred to as an olefin cracking process (OCP).

Catalysts comprising molecular sieve, particularly aluminosilicate-comprising catalysts, and more particularly zeolite-comprising catalysts, have the further advantage that in addition to the conversion of methanol or ethanol, these catalysts also induce the conversion of olefins to ethylene and/or propylene. Therefore, aluminosilicate-comprising catalysts, and in particular zeolite-comprising catalysts, are particularly suitable for use as the catalyst in an OCP. Particular preferred catalysts for the OCP reaction, i.e. converting part of the olefinic product, and preferably part of the C4+ hydrocarbon fraction of the olefinic product including C4+ olefins, are catalysts comprising at least one zeolite selected from MFI, MEL, TON and MTT type zeolites, more preferably at least one of ZSM-5, ZSM-11, ZSM-22 and ZSM-23 zeolites.

Both the OTO process and the OCP may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

The catalyst can deactivate in the course of the OCP and OTO process. The deactivation occurs primarily due to deposition of carbonaceous deposits, such as coke, on the catalyst by side reactions. The deactivated catalyst can be regenerated to remove a portion of the carbonaceous deposit by methods known in the art. It is not necessary, and indeed may be undesirable, to remove all the carbonaceous deposit from the catalyst as it is believed that a small amount of residual carbonaceous deposit such as coke may enhance the catalyst performance. Additionally, it is believed that complete removal of the carbonaceous deposit may also lead to degradation of the molecular sieve.

The same catalyst may be used for both the OTO process and OCP. In such a situation, the catalyst comprising molecular sieve, particularly comprising aluminosilicate molecular sieve and more particularly comprising zeolite, may be first used in the OCP reaction zone for the conversion of the C4+ olefins of the C4+ hydrocarbon fraction. The catalyst from the OCP may then be used, typically without regeneration, in the OTO process for conversion of an oxygenate feedstock and an olefinic co-feed. The deactivated catalyst from the OTO process may then be regenerated as described herein, and the regenerated catalyst then used again in the OCP.

This line-up may be beneficial because it provides good heat integration between the OCP, OTO and regeneration processes. The OCP is endothermic and at least a portion of the heat of reaction can be provided by passing catalyst from the regeneration zone to the OCP reaction zone, because the regeneration reaction which oxidizes the carbonaceous deposits from the loaded catalyst is exothermic.

Embodiments of the present invention will now be described by way of example only and with reference to the accompanying non-limiting figures.

Figure 1:
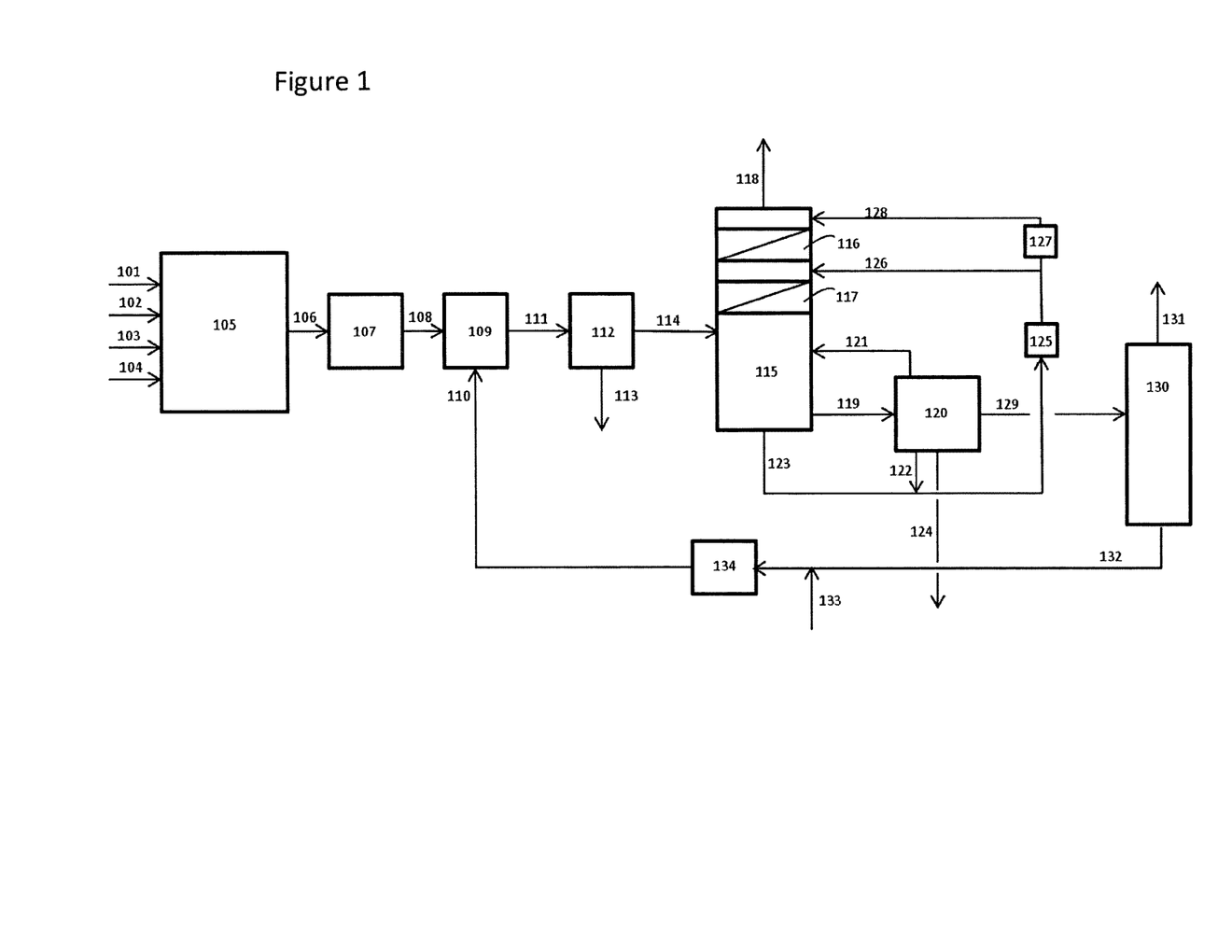
FIGS. 1 to 4 are schematic diagrams of exemplary, but non-limiting, embodiments of a process for the preparation of an olefinic product as described herein.

FIG. 1 exemplifies an embodiment of the present invention. An oxygenate feedstock 101 is fed into the oxygenate reaction zone 105. An oxygenate co-feed 102 may also be supplied by an oxygenate recovery stream. A diluent 103 may also be provided to the reaction zone. Preferably, an olefinic co-feed 104 is also provide to the reaction zone. The oxygenate co-feed, diluent and olefinic co-feed may be supplied to the reaction zone separately or one or more of these streams may be combined with the oxygenate feedstock or together before being fed to the reaction zone.

In the oxygenate (or OTO) reaction zone 105, reaction is carried out in the presence of a catalyst at a temperature in the range of from 350 to 1000° C. Following reaction, the gaseous product is separated from the bulk of the catalyst to produce a reaction effluent stream 106. The reaction effluent stream is cooled in one or more heat exchangers 107 situated in series, to provide a cooled reaction effluent stream 108 at a temperature greater than the dew point temperature of the reaction effluent stream and preferably in the range of from 150 to 250° C. An aqueous liquid 110 is directly injected into the cooled reaction effluent stream through a quench fitting (e.g. a spray nozzle) 109, rapidly cooling said stream by mixing it with a large quantity of water to a temperature below the dew point temperature of the reaction effluent stream.

The resultant quench effluent stream 111 is preferably at a temperature in the range of from 60 to 95° C. and is fed into a quench tower 112 containing internal and/or packing 113 and 114.

At least one second aqueous liquid stream 124, 126 is fed into the quench tower above the internals and/or packing.

An aqueous stream 120 is removed from the bottom of the quench tower 112 and cooled in air or water coolers 123 and 125 to provide the second aqueous liquid streams 124, 126.

In the embodiment of the invention exemplified in FIG. 1, a liquid stream 116 is removed from the bottom of the quench tower and passed to the separation vessel 117. A gaseous stream 118 is optionally returned to the quench tower 112. Aqueous material 119 is added to the aqueous stream for recycle. A solid stream 121, preferably in the form of a slurry, may be removed and the catalyst solids therein may be recycled. Liquid hydrocarbon stream 122 may be separated as a waste stream or for use as fuel.

An oxygenate containing liquid stream 127 is separated and passed to an oxygenate separation zone 128 to produce an oxygenate recovered stream 129, which may be used as oxygenate co-feed 102 and an aqueous stream, which after cooling in an air or water cooler 131, can be re-used as the first aqueous liquid 110.

A quench tower gas stream 115 comprising the olefinic product is removed from the top of the quench tower.

A basic material, for instance a caustic solution, 132 may be added into the process to prevent the lowering of the pH due to the accumulation of acids in the recycle streams.

Figure 2:
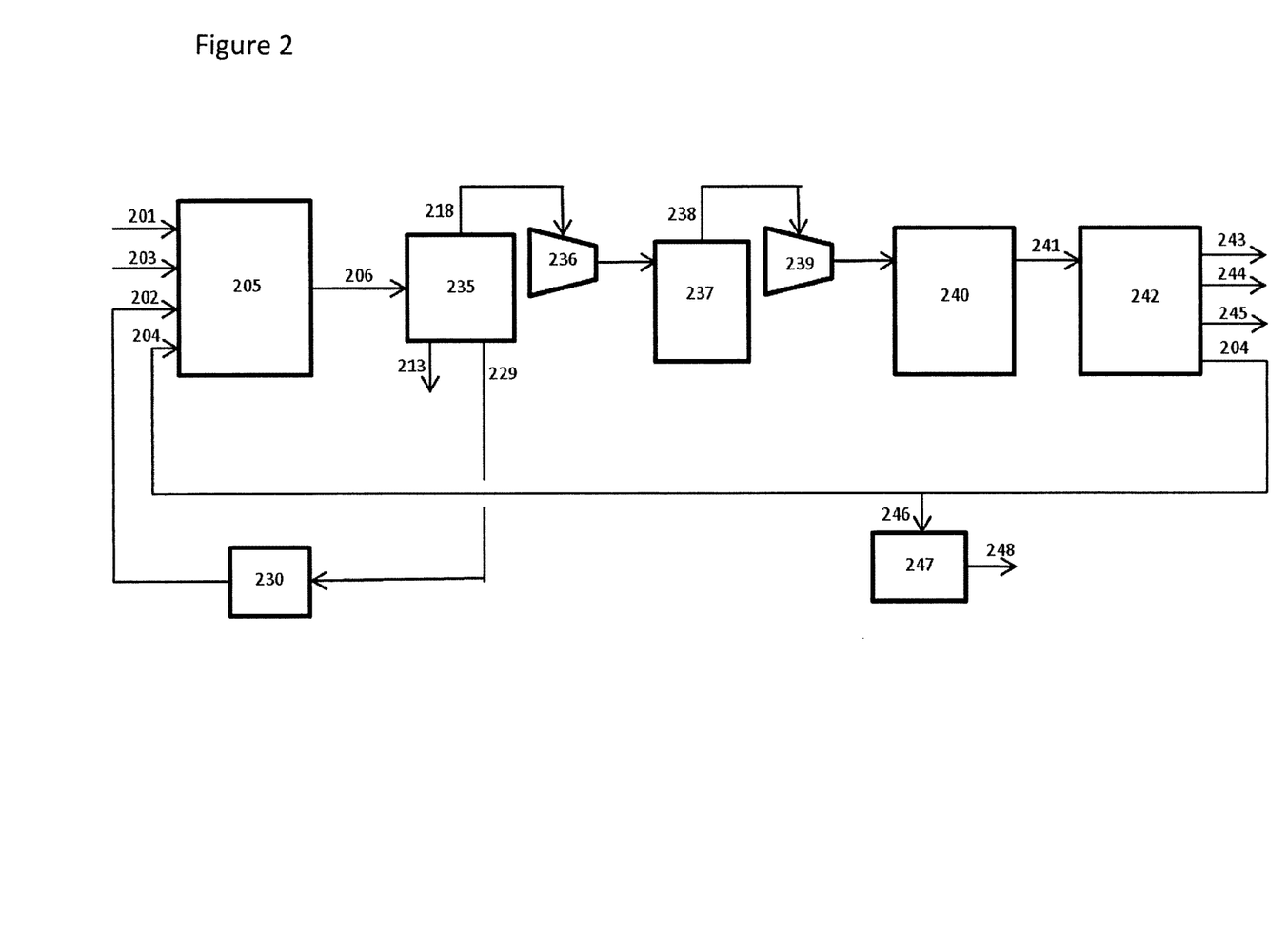

FIG. 2 shows one possible embodiment of the invention as it is incorporated into an overall process for the production of olefinic products such as ethylene and propylene. Oxygenate feedstock 101, an oxygenate co-feed 102, a diluent 103 and an olefinic co-feed 104 are provided to an oxygenate reaction zone 105. Reaction is carried out in the presence of a catalyst at elevated temperatures. The reaction product is separated from the catalyst to provide reaction effluent stream 106. The cooling and initial separation of steps (b), (c) and (d) of the present invention are carried out one or more times in series or in parallel to provide a quench tower gas stream 215. An oxygenate containing liquid stream 227 is also produced and can be subjected to separation and purification in the oxygenate separation zone 228 before being recycled as the oxygenate co-feed 102. A solid stream 221 is also produced.

The quench tower gas stream 215 is compressed in one or more gas compressors 234 and is then passed to a carbonyl compound absorption zone 235 in which the stream is treated with a caustic solution to remove carbon dioxide and carbonyl compounds. The resultant stream 236 is further compressed in one or more compressors 237 before being passed to water removal zone 238. After water removal, the remaining gas stream enters an olefin separation zone 240 to be separated, preferably by one or more cryogenic distillation processes, to provide two or more olefinic component streams 241, 242, 243 and 104, including a stream comprising C4+ olefins which is recycled as olefinic co-feed 104.

In one alternative embodiment, all or part 244 of this stream is subjected to an OCP 245 to provide a stream comprising ethylene and propylene 246. This stream 246 can then be fed back into the process as part of olefin rich gas stream 215.

Figure 3:
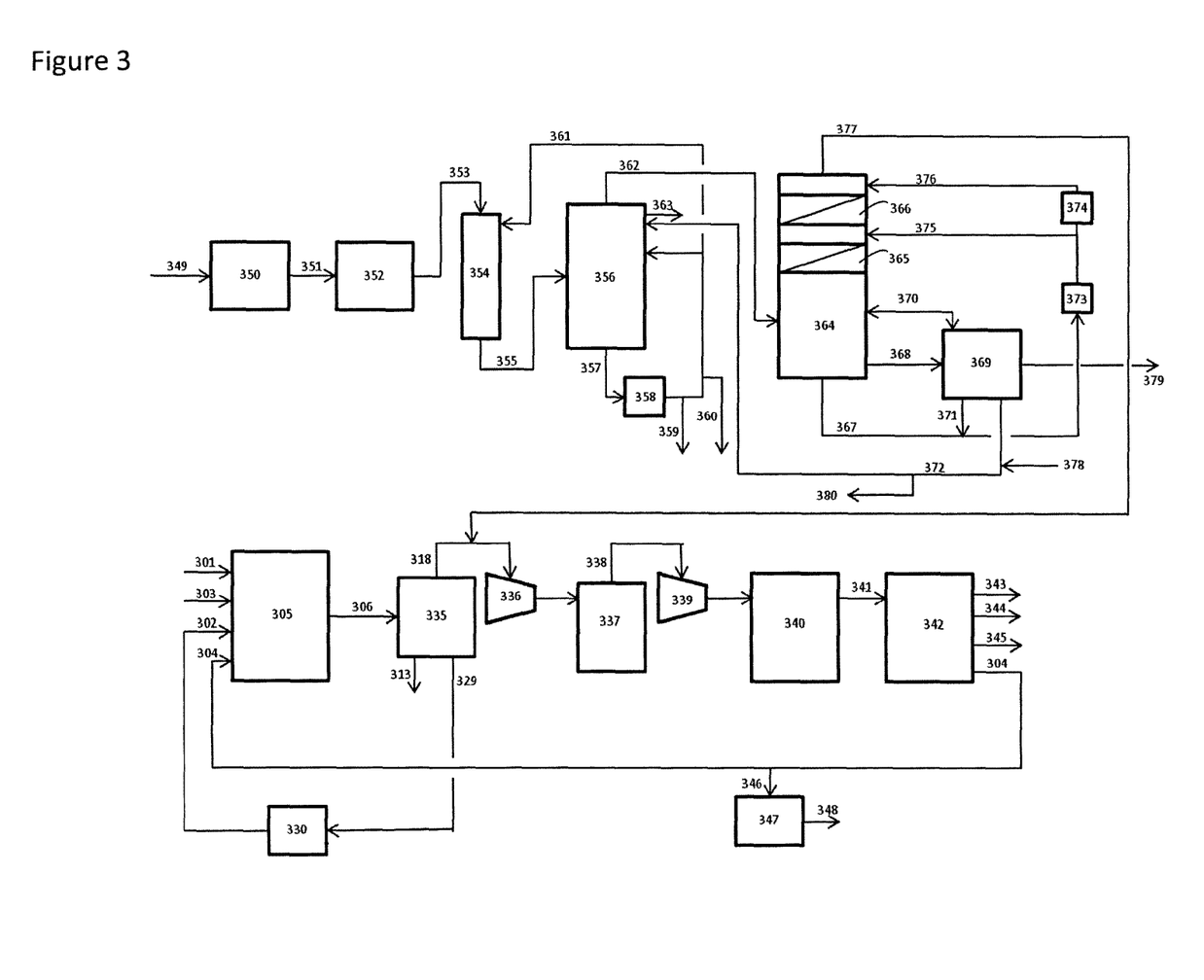

FIG. 3 shows an embodiment of the present invention wherein it is combined with a process for producing an olefinic product by naphtha cracking.

Feed stream 347, comprising any, preferably paraffinic, feedstocks within the boiling range of propane, butane, naphtha, NGL (natural gas liquid), condensate, kero, gas oil or hydrowax, is subjected to cracking in one or more pyrolysis furnaces/reactors 348, by heating at a temperature in the range of from 750 to 900° C. The cracked effluent product stream is produced in a multitude of parallel coils in one pyrolysis furnace. The cracked effluent is cooled in one or more parallel transfer line exchangers per furnace. In FIG. 3, stream 349 represents all cracked effluent product streams of all furnaces. Each furnace has one or more transfer line exchangers in series 350, which cool the temperature down to in the range of from 300 to 650° C. The thus-cooled stream 351 is subjected to an oil quench via quench fitting 352 to further reduce the temperature to in the range of from 150 to 270° C. One or more streams 353 produced in this manner are then fed to a gasoline fractionator 354. A bottoms stream 355 of the gasoline fractionator is removed and passed through a heat exchanger, before being recycled to the fractionator or used as the oil quench 359. Side product streams including ECR (ethylene cracked residue being stripped using quench oil) 357, CGO (cracked gas oil) and solids/coke 358 can be removed from the bottoms stream. Optionally, a side stream CGO 386 can be produced from the gasoline fractionator.

A gaseous stream 360 is removed from the top of the gasoline fractionators and fed to a quench tower 361, containing one or more sets of internals (362 and 363). An aqueous stream 364 is removed from the bottom of the quench tower and is recycled 372, 373 after cooling in air or water cooled heat exchangers 370, 371. A side draw 365 from the quench tower is fed to separation vessel 366 providing a gaseous stream 367, a recycle aqueous stream 368, a gasoline-containing stream 369, which is fed back into the gasoline fractionators 354, with an optional bleed 377, and a process water stream 376 for further processing. The olefin rich quench tower overhead stream 374 can be combined with the quench tower gas stream 215 from the OTO process.

Figure 4:
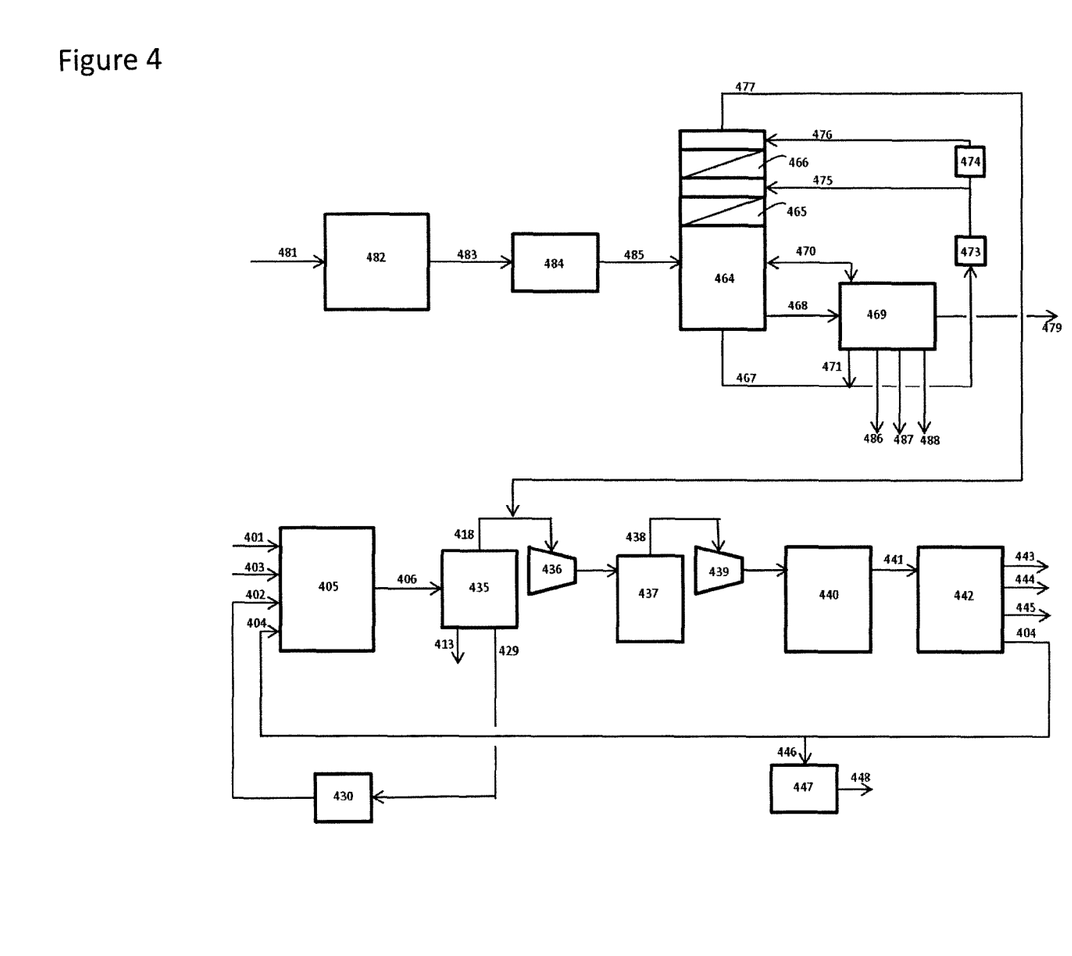

FIG. 4 shows an embodiment of the present invention wherein it is combined with a process for producing an olefinic product by ethane or ethane/propane cracking.

Ethane or ethane/propane feed 478 is provided to one or more parallel pyrolysis furnaces/reactors 4479 and heated at a temperature in the range of from 800 to 950° C. Each pyrolysis furnace has parallel transfer line exchangers. Each pyrolysis furnace can have one or more transfer line exchangers in series. The effluent gas stream 480 represents the furnace effluent from all pyrolysis furnaces. The furnace effluent is cooled to a temperature in the range of from 180 to 320° C. in one or more heat exchangers 481 in series. One or more gas streams 482 produced by this method are combined and fed to a quench tower 461 containing internals 462 and 463. The quench tower is operated as described for FIG. 3. In the separator 466, coke 483, heavy oil/pitch 484 and pygas/gasoline 485 streams are separated for processing and/or use elsewhere.

It should be noted herein that, in the numbers on FIGS. 1-4 and referred to in the text, corresponding features on different Figures will have the same second and third digits in their indicative numbers, with the first digit referring to that Figure number. Thus, number 361 and 461 will refer to the same feature in FIGS. 3 and 4, respectively.

Figure 5:
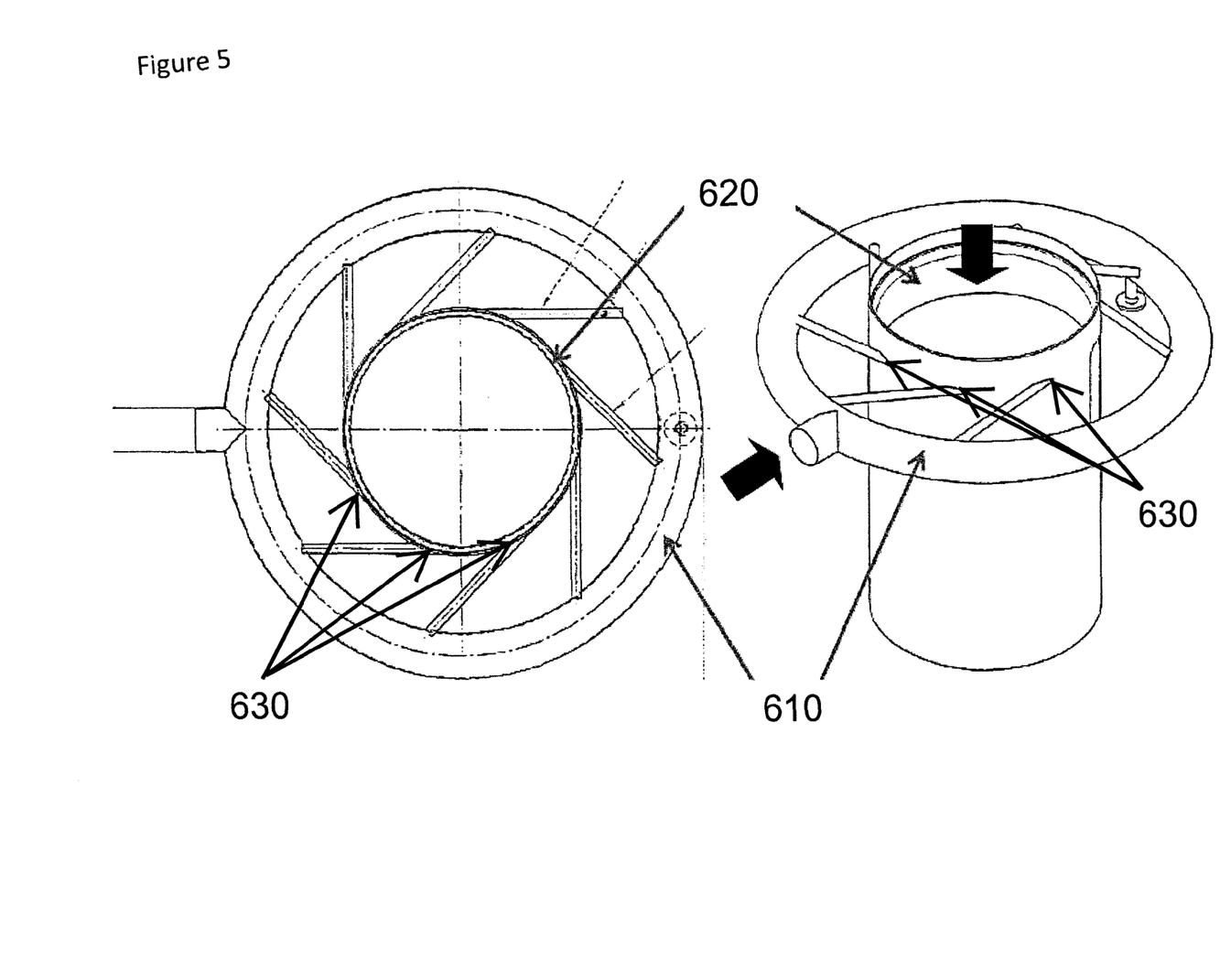
FIG. 5 provides 2 views (5A and 5B) of an embodiment of a quench fitting.

FIG. 5 uses a different numbering scheme than FIGS. 1-4 and the items in this Figure are not related by number to any of the previous Figures. FIG. 5 depicts an embodiment of a direct quench fitting with two views, 5A and 5B. FIG. 5A shows a top view of a direct quench fitting. The quench ring 610 is concentric to the effluent conduit 620 and the direct quench points 630 are located at a plurality of points around the effluent conduit. The direct quench points may be spray nozzles or another type of injection device for injecting the aqueous liquid into the effluent conduit FIG. 5B shows a side view of the quench ring 610, the effluent conduit 620 and the direct quench points 630.

That which is claimed is:

1. A process for the preparation of an olefinic product, the process comprising the steps of:
   (a) reacting an oxygenate feedstock, comprising oxygenate, in an oxygenate reaction zone in the presence of a catalyst comprising a molecular sieve, at a temperature in the range of from 350 to 1000° C., to produce a reaction effluent stream, comprising at least oxygenate, olefin, water and acidic by-products;
   (b) cooling the reaction effluent stream by means of an indirect heat exchange to a temperature greater than the dew point temperature of reaction effluent stream;
   (c) further rapidly cooling the heat exchanged reaction effluent stream to a temperature lower than the dew point temperature of the reaction effluent stream by direct injection of an aqueous liquid into a conduit transporting the reaction effluent stream from the heat exchange of step (b) to the quench tower of step d), to form a quench effluent stream; and
   (d) passing the quench effluent stream into a quench tower and contacting the quench effluent stream with a second aqueous liquid in the presence of at least one set of quench tower internals, to produce a quench tower gaseous stream comprising the olefinic product wherein in step (c) the aqueous liquid is injected by means of a quench fitting.

2. The process as claimed in claim 1, wherein in step (b) the reaction effluent stream is cooled to a temperature in the range of from 140° C. to 370° C.

3. The process as claimed in claim 1, wherein the quench fitting comprises a spray nozzle.

4. The process as claimed in claim 1, wherein in step (c) the heat exchanged reaction effluent stream is cooled such that the quench effluent stream is at a temperature in the range of from 30 to 100° C.

5. The process as claimed in claim 1, wherein in step (c) the heat exchanged reaction effluent stream is cooled such that the first quench effluent stream is at a temperature in the range of from 50 to 150° C.

6. The process as claimed in claim 1, wherein the quench tower contains at least one set of internals and one set of packing.

7. The process for the preparation of an olefinic product, said process comprising preparing an olefin rich gas stream according to the process of claim 1 and combining it with a further olefin rich gas stream obtained from a cracking process to form a combined olefin rich gas stream.

8. The process as claimed in claim 7, wherein the further olefin rich gas stream is obtained from a naphtha cracking process comprising the steps of:
(a) heating a feed comprising a feedstock within the boiling range of propane, butane, naphtha, NGL, condensate, kero, gas oil or hydrowax at a temperature in the range of from 750 to 900° C. in a pyrolysis furnace to produce a naphtha furnace effluent stream;
(b) cooling the naphtha furnace effluent stream by means of an indirect heat exchange to a temperature in the range of from 300 to 650° C.;
(c) further rapidly cooling the naphtha furnace effluent stream to a temperature in the range of from 150 to 270° C. by direct injection of an oil into the naphtha furnace effluent stream to produce an oil-quenched effluent stream;
(d) treating the oil quenched effluent stream in a fractionator to produce a fractionated gaseous stream; and
(e) subsequently contacting the fractionated gaseous stream with an aqueous stream in a quench section to produce the further olefin rich gas stream.

9. The process as claimed in claim 7, wherein the further olefin rich gas stream is obtained from an ethane or ethane/propane cracking process comprising the steps of:
(a) heating a feed comprising ethane and/or propane at a temperature in the range of from 800 to 950° C. in a pyrolysis furnace to produce an ethane furnace effluent stream;
(b) cooling the ethane furnace effluent stream to a temperature in the range of from 180 to 320° C. in one or more heat exchangers in series; and
(c) contacting the resultant ethane furnace effluent stream with an aqueous stream in a quench tower to produce the further olefin rich gas stream.

10. The process for the production of an olefinic product according to claim 7, wherein the combined olefin rich gas stream is purified and separated by a process comprising the steps of:
(a) compressing the combined olefin rich gas stream;
(b) treating the compressed stream with a caustic solution to absorb carbon dioxide and carbonyl compounds;
(c) further compressing the stream produced in step (b);
(d) removing water from the stream produced in step (c); and
(e) separating the stream produced in step (d) into olefinic products by means of cryogenic distillation.

* * * * *